United States Patent [19]
Brugger

[11] Patent Number: 5,383,785
[45] Date of Patent: Jan. 24, 1995

[54] PUSH-BUTTON OPERATED CHUCKING DEVICE FOR A DENTAL ANGLE PIECE

[75] Inventor: Wilhelm Brugger, Anthering, Austria

[73] Assignee: Dentalwerk Burmoos Gesellschaft m.b.H., Burmoos, Austria

[21] Appl. No.: 104,800

[22] Filed: Aug. 11, 1993

[30] Foreign Application Priority Data

Aug. 12, 1992 [AT] Austria ................. 1626/92

[51] Int. Cl.⁶ ............................................. A61C 1/14
[52] U.S. Cl. ......................................................... 433/129
[58] Field of Search ....................... 433/126, 127, 129; 279/43.1, 43.7, 46.4, 50

[56] References Cited

U.S. PATENT DOCUMENTS

| 287,761 | 10/1883 | Gilbert | 433/129 |
| 2,263,808 | 11/1941 | Hutchinson | 279/46.4 |
| 3,631,597 | 1/1972 | Lieb et al. | 433/129 |
| 5,254,004 | 10/1993 | Feldman et al. | 433/129 |

FOREIGN PATENT DOCUMENTS

| 373488 | 1/1984 | Austria . | |
| 3448 | 10/1984 | Austria . | |
| 0098754 | 1/1984 | European Pat. Off. . | |
| 0420169 | 4/1991 | European Pat. Off. . | |
| 1248229 | 8/1967 | Germany | 433/127 |
| 2905484 | 8/1979 | Germany . | |

*Primary Examiner*—Cary E. O'Connor
*Attorney, Agent, or Firm*—Friedrich Kueffner

[57] ABSTRACT

A chucking device for holding a dental tool by a collet chuck with collet chuck sleeve, wherein the collet chuck can be released by a push button against the force of clamping spring. The collet chuck sleeve has at both ends thereof axial slots, so that it is constructed at both ends as a collet chuck. The casing of the collet chuck is undercut at both ends, wherein the undercut at the side of the tool is mounted in an axially fixed, but rotating conical seat and the undercut on the side of the push button is mounted in a conical seat of an actuating member. The actuating member is under the influence of the clamping spring and, for releasing the collet chuck, the actuating member is displaceable against the force of the clamping spring toward the axially fixed seat. Instead of the collet chuck, it is also possible to provide two axially spaced apart groups of radially displaceable clamping elements.

5 Claims, 1 Drawing Sheet

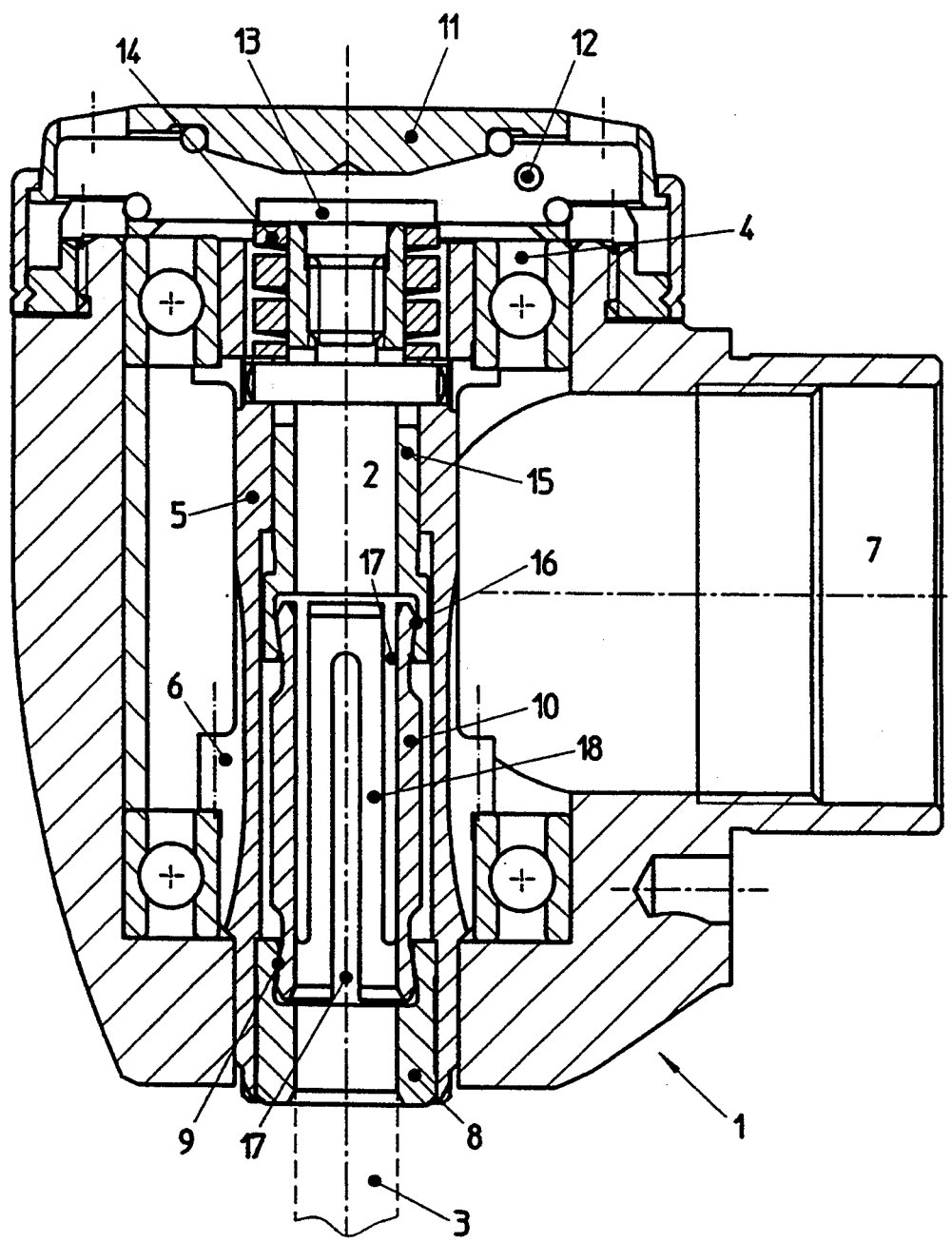

PUSH-BUTTON OPERATED CHUCKING DEVICE FOR A DENTAL ANGLE PIECE

BACKGROUND OF THE INVENTION

1. Field of the Invention

The present invention relates to a push button-operated chucking device for a dental angle piece including clamping elements which press radially against the tool shaft for holding the tool shaft in a frictionally engaging manner. By axially moving an actuating member connected to the push button, and in interaction with a conical control surface, the clamping elements can be moved radially outwardly and inwardly for releasing and clamping the tool shaft.

2. Description of the Related Art

Chucking devices of the above-described type are known in various embodiments.

For example, from DE-C-2 29 05 484 and AT-B 373 488, it is known in the art to support the tool by means of a collet chuck which can be preferably released against the force of a spring by means of a push button arranged at an axial distance from the tool. The chucking action is obtained by the spring in interaction with a conical control surface for the outer side of the collet chuck.

In the device according to DE-C-2 29 05 484, the chucking area is located seen in axial direction near the tool end, i.e., on the side of the push button, while in the device known from AT-B 373 488 the chucking area is near the opening for inserting the tool.

Other means for fixing angle pieces in a frictionally engaging manner are also known in the art. For example, in accordance with Austrian Patent Application A 3448/84, a holding element which is elastic in radial direction by means of a slotted sleeve whose internal radius is smaller than the shaft radius, enlarges its internal radius by the approach of two conical control surfaces, and, thus, releases the tool.

A similar type of support has become known from EP-A1-0 098 754. However, in this case, the change of the radius is achieved only by means of a conical surface.

A different type of fixing device with frictional engagement has become known from EP-A10 420 169. A helical spring mounted in a holder is wound around a clamping member which is slotted in axial direction and presses the clamping member against the tool shaft. When an axial pressure is exerted on the spring, the internal radius of the spring is enlarged and the shaft is released.

All of the above-discussed collet chucks have the significant disadvantage that the axial area in which the shaft is actually clamped, i.e., the clamping area, is relatively short. In addition, in the relatively long axial area in which the collet chucks do not rest against the tool shaft, the tool shaft is guided in a bore of the chucking sleeve, i.e., the guide length, which must have at least a diameter which corresponds to the largest possible diameter of the tool shaft due to tolerances. Since the bore itself is also subject to a tolerance, there is in practically all types of applications a play which may be small, but which is still noticeable because of the high rates of rotation which occur. This play is harmful to the tool and to the handpiece and is unpleasant or even painful to the patient, because it causes wobbling of the tool in its support.

The fixing device according to EP-A1-0 420 169 has the additional disadvantage that during clamping not only the desired decrease of the internal radius of the spring occurs, but also an undesirable increase of the outer diameter thereof, so that, although the tool does not wobble in the clamping sleeve, the spring including tool and clamping sleeve wobbles in the holder. As a result, in spite of the relatively great axial length of clamping between tool and clamping sleeve, fixing with respect to the angle piece again takes place only at one axial location.

Accordingly, all chucking devices have the decisive disadvantage that there is a large difference between the clamping length, i.e., length of contact with the clamping elements, and the guiding length, i.e., insertion length minus clamping length, which facilitates wobbling.

Fixing devices which eliminate this problem have already been proposed in dental hand pieces in which the tool axis coincides with the principal axis of the handpiece and, thus, the axial extension of the tool holder does not play a role.

Thus, AT-B 300 176 discloses a handpiece which includes a double collet chuck which clamps the tool shaft at two axially spaced apart locations. Of course, because of the coaxial arrangement of drive axis and tool axis, the actuation of this collet chuck is only possible by means of complicated rotating mechanisms.

An even more complicated mechanism is disclosed by DD-PS 118 800 because releasing and clamping of the double collet chuck is effected by means of a tilting lever which also rotates in the interior of the handpiece, so that higher rates of rotation are not possible.

Another double collet chuck is known from U.S. Pat. No. 3,631,597. However, in this double collet chuck, only one end is utilized for clamping the tool shaft, while the other end is used for axially fixing the collet chuck.

The use of a true double collet chuck is known from EP-A1-0 421 907. It is a true double collet chuck because it chucks as a result of an axial compression spring and not because of its own elasticity, and because it releases the tool shaft when the spring force is exceeded. As a result, it is possible to clamp the tool shaft at two locations which are axially spaced apart from each other. This double collet chuck has the disadvantage that, although the use of simple conventional conical counterpieces is possible, a lever mechanism for reversing the movement must be provided for the push button because of the construction of the collet chuck as a cylindrical sleeve with two hollow truncated cones which are mounted on the cylindrical sleeve and narrow in axial direction. In addition, the naturally flexible collet chuck has the tendency to buckle under compressive load at high rates of rotation, so that the collet chuck must be guided as exactly as possible along its entire external area.

SUMMARY OF THE INVENTION

Therefore, it is the primary object of the present invention to eliminate the above-described shortcomings of the angle pieces having two axially spaced apart clamping locations and an actuation by means of a push button, and to provide a fixing device in which the above-described disadvantages do not occur.

In accordance with the present invention, clamping elements are provided at two locations which have an axially fixed distance from each other, wherein the actuating member acts on both groups of clamping elements in such a way that it has the tendency to move them apart from each other in axial direction, and wherein a conical control surface is provided for each group of clamping elements, wherein at least one control surface is axially displaceable by means of the actuating member.

The measures provided by the present invention have the result that the tool is clamped at two axially spaced apart locations, so that the seat of the tool is significantly improved and a simple actuating mechanism can be used and an improved dynamic behavior is achieved because of the tensile load acting between the two clamping locations.

When a double collet chuck is used, the clamping elements are the resilient tongues of the double collet chuck. During operation, the double collet chuck is subjected to axial tension in a favorable manner. The push button can be constructed without a complicated reversing mechanism and can act directly on the end of the spring facing the push button. The two ends of the double collet chuck are each provided with a conical portion supported in an undercut ring, wherein the tips of the conical portions are directed toward each other.

When two groups of axially spaced apart and radially movable clamping elements are used, these clamping elements are mounted, for example, in a common sleeve. The conical control surface of the group of clamping elements located on the side of the push button is pulled toward the push button by the spring and the tensile force is transmitted through the sleeve to the group of clamping elements on the side of the tool, wherein the clamping elements on the side of the tool rest against an axially fixed conical control surface.

In accordance with a preferred embodiment, the clamping elements are tongues of a collet chuck which has axial slots at both ends thereof. As a result, the collet chuck is constructed as a collet chuck at both ends thereof. In addition, the outer casing of the collet chuck is undercut at both ends to form the conical surfaces, so that clamping occurs during tensile loads, wherein the undercut on the side of the tool is mounted in an axially fixed conical seat which rotates together with the tool and the undercut on the side of the push button is mounted in a conical seat of the actuating member which is under the influence of a clamping spring and is movable by the push button against the force of this clamping spring in the direction toward the axially fixed seat.

Because of the flying arrangement of the collet chuck between the two conical seats, it is possible to almost double the holding force of the tool while the force and characteristic of the collet chuck spring remains the same.

Because of the novel configuration of the collet chuck which fixes during tension and releases without pressure, it is possible to substantially reduce the wall thickness of the collet chuck sleeve.

Another advantage of this configuration is the fact that the length of the bore of the tool receiving means which must be produced precisely is substantially reduced or can even be produced with a slightly excess dimension which advantageously influences the manufacturing costs.

The various features of novelty which characterize the invention are pointed out with particularity in the claims annexed to and forming a part of the disclosure. For a better understanding of the invention, its operating advantages, specific objects attained by its use, reference should be had to the drawing and descriptive manner in which there are illustrated and described preferred embodiments of the invention.

BRIEF DESCRIPTION OF THE DRAWING

In the drawing:

The single figure of the drawing is a schematic sectional view of a tool receiving means provided with a collet chuck according to the present invention.

DESCRIPTION OF THE PREFERRED EMBODIMENT

As illustrated in the drawing, a dental tool holder with tool holder head 1 is provided with a receiving means 2 for a tool 3 which is only illustrated in broken lines. The receiving means is mounted in ball bearings 4 and has a drive sleeve 5 whose teeth 6 can be placed in engagement with a drive, not shown, on the side 7 of the head 1 facing the handpiece.

Mounted in the interior of the drive sleeve 5 on the end facing the tool is a support ring 8 which rotates together with the drive sleeve 5 and which, on the side facing the head 1, has a conical undercut 9. The collet chuck 10 constructed according to the present invention engages in this undercut 9 with its end facing the tool.

A push button 11 of the known type is mounted on the upper side of the head 1. The push button 11 is under the influence of the force of a button-type spring 12 and, thus, is spaced apart from an actuating member 13 which is under the influence of a collet chuck spring 14 and rotates together with the drive sleeve 5. The actuating member 13 is connected to a sleeve 15 or is integrally manufactured with the sleeve 15. As a result, the sleeve 15 is forced toward the push button 11 under the influence of the collet chuck spring 14 and, by means of a conical undercut 16 which is similar to the undercut 9 but is directed in the opposite direction, engages the end of the collet chuck 10 on the side of the push button and also tends to move it toward the push button 11.

The end of the collet chuck 10 on the side of the push button is constructed analogously to the end facing the tool. In other words, slots 17 are provided which permit a resilient deformation of the collet chuck in such a way that the distances between radially oppositely located collet chuck ends becomes smaller. The slots 17 on the end facing the push button are offset, preferably symmetrically offset, relative to the slots 17' of the end of the collet chuck facing the tool. As a result, the collet chuck in its totality is composed of axial parts 18 which are connected to each other alternatingly at the ends facing the push button and at the ends facing the tool, so that a closed zig-zag configuration is formed along a cylindrical casing.

Since the force of the collet chuck spring 14 is transmitted through the sleeve 15 and the conical seat 16 to the collet chuck 10 and further through the conical seat 9 to the axially fixed ring 8, the clamping force after resting against the tool shaft has been effected and, thus, in the stationary state and in the state of operation is equal to the clamping force in known collet chucks which, instead of the conical seat 16, either have a single-piece transition to the sleeve 15 or are fixedly connected to the sleeve 15 by means of a collar or the like.

The present invention is not limited to the embodiment illustrated in the drawing. For example, it is possible that the collet chuck has a longer or shorter length, wherein it is advantageous to provide such an axial distance between the two clamping ends of the collet chuck that even larger moments can be absorbed without the occurrence of large individual lateral forces. Also, within certain limits determined by the size and use of the collet chuck, the number of axial tongues or parts 18 of the collet chuck can be freely selected. It may even be possible to provide a collet chuck which is axially divided. However, this does not change the construction according to the present invention which provides two clamping collet chuck ends which are arranged coaxially but directed against each other, wherein the two collet chuck ends are arranged at an invariable distance from each other and which are acted upon by the force of a single spring.

It is also possible to further extend the collet chuck and to arrange the clamping spring between the rings with the conical control surfaces which engage the collet chuck ends and radially outwardly of the collet chuck sleeve. In this case, the actuating mechanism acts directly on one of the rings and compresses the clamping spring by means of this ring.

The invention is not limited by the embodiments described above which are presented as examples only but can be modified in various ways within the scope of protection defined by the appended patent claims.

I/We claim:

1. A chucking device comprising a collet chuck for holding a dental tool, the collet chuck comprising a collet chuck sleeve, the collet chuck sleeve having two ends, the collet chuck sleeve having axial slots at both ends thereof, the chucking device further comprising a push button for releasing the collet chuck against the force of a clamping spring, the collet chuck sleeve having at both ends in the areas of the axial slots conical undercuts, wherein one of the undercuts is mounted in a conical seat which is mounted so as to be axially fixed and rotating together with the dental tool, an actuating member biased by the clamping spring, another of the conical undercuts being mounted in a conical seat of the actuating member, the actuating member being axially displaceable by means of the push button against the axially fixed seat.

2. The chucking device according to claim 1, wherein the axial slots at the two ends of the collet chuck sleeve are arranged offset relative to each other in circumferential direction.

3. The chucking device according to claim 2, wherein the axial slots overlap each other in axial direction.

4. A chucking device for holding a dental tool having a shaft in an angle piece, the chucking device comprising two groups of radially movable clamping elements arranged at an axially fixed distance from each other, a spring for pressing the clamping elements against the tool shaft, an actuating member acting on both groups of clamping elements such that the actuating member acts on both groups of clamping elements in axial directions directed axially apart from each other, wherein a conical control surface is arranged for each group of clamping elements, wherein at least one of the control surfaces is axially displaceable by the actuating member.

5. The chucking device according to claim 4, wherein the radially movable clamping elements are mounted in a common sleeve, further comprising a push button, wherein the conical control surface of the group of clamping elements on the side of the push button is pulled toward the push button by means of the spring, and wherein the pulling force is transmitted through the common sleeve to the group of clamping elements on the side of the tool, and wherein the group of clamping elements on the side of the tool rests against an axially fixed conical control surface.

* * * * *